US 6,733,767 B2

(12) United States Patent
Chern et al.

(10) Patent No.: US 6,733,767 B2
(45) Date of Patent: *May 11, 2004

(54) LIQUID POLYMERIC COMPOSITIONS FOR CONTROLLED RELEASE OF BIOACTIVE SUBSTANCES

(75) Inventors: Rey T. Chern, Harteyville, PA (US); Joel R. Zingerman, Doylestown, PA (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/271,098

(22) Filed: Mar. 18, 1999

(65) Prior Publication Data

US 2002/0064547 A1 May 30, 2002

Related U.S. Application Data

(60) Provisional application No. 60/079,574, filed on Mar. 19, 1998.

(51) Int. Cl.⁷ ................................................ A61K 9/00
(52) U.S. Cl. .................. 424/426; 424/424; 424/425; 424/422; 424/457; 424/458; 424/459; 424/489; 424/423; 604/891.1
(58) Field of Search ................. 424/426, 424, 424/425, 422, 457, 458, 459, 489, 423; 604/891.1

(56) References Cited

U.S. PATENT DOCUMENTS 2,562,830 A   7/1951  Stenzl
3,337,570 A   8/1967  Sherlock et al.

(List continued on next page.)

FOREIGN PATENT DOCUMENTS

| EP | 0002916 | * | 7/1979 | .......... A61K/31/34 |
| EP | 0007812 | * | 2/1980 | .......... C07H/17/08 |
| EP | 0179022 | * | 4/1986 | .......... C07C/127/22 |
| EP | 0295117 | * | 12/1988 | .......... C07D/231/44 |
| EP | 0508699 | * | 10/1992 | .......... C07H/17/08 |
| EP | 0 537 559 |   | 4/1993 |   |
| EP | 0846686 | * | 6/1998 | .......... C07D/231/38 |
| EP | 892 060 | * | 1/1999 | .......... C12N/15/54 |
| GB | 1 390 336 |   | 4/1975 |   |
| GB | 2 140 010 |   | 11/1984 |   |
| NZ | 237 086 |   | 7/1993 |   |
| WO | WO9629073 | * | 9/1996 | .......... A61K/31/40 |

OTHER PUBLICATIONS

Reminton; the science and practice of pharmacy P. 1517, 1995.*
Reminton: The Science and Practice of Pharmacy, 19ᵗʰ edition, 1995, p. 710–711.*

(List continued on next page.)

Primary Examiner—Russell Travers
Assistant Examiner—Shahnam Sharareh
(74) Attorney, Agent, or Firm—Mitul I. Desai; David L. Rose

(57) ABSTRACT

Controlled release of hydrophobic bioactive substances in vivo over an extended time period and without "bursts" of drug release is achieved using a liquid polymeric composition including a polymer such as poly(lactide-co-glycolide) copolymer in a mixture of hydrophilic and lipophilic solvents.

16 Claims, 3 Drawing Sheets

U.S. PATENT DOCUMENTS

| | | |
|---|---|---|
| 3,748,356 A | 7/1973 | Wellinga et al. |
| 3,904,682 A | 9/1975 | Fried et al. |
| 3,950,360 A | 4/1976 | Aoki et al. |
| 4,009,197 A | 2/1977 | Fried et al. |
| 4,072,716 A | 2/1978 | Sauer et al. |
| 4,150,108 A | 4/1979 | Graham |
| 4,199,569 A | 4/1980 | Chabala et al. |
| 4,225,598 A | 9/1980 | Brechbuhler et al. |
| 4,233,299 A | 11/1980 | Trummlitz et al. |
| 4,283,400 A | 8/1981 | von Bittera et al. |
| 4,294,753 A | 10/1981 | Urist |
| 4,310,519 A | 1/1982 | Albers-Schonberg et al. |
| 4,329,332 A | 5/1982 | Couvreur et al. |
| 4,331,652 A | 5/1982 | Ludwig et al. |
| 4,333,919 A | 6/1982 | Kleber et al. |
| 4,389,330 A | 6/1983 | Tice et al. |
| 4,427,663 A | 1/1984 | Mrozik |
| 4,455,256 A | 6/1984 | Urist |
| 4,468,390 A | 8/1984 | Kitano |
| 4,489,055 A | 12/1984 | Couvreur et al. |
| 4,526,909 A | 7/1985 | Urist |
| 4,526,938 A | 7/1985 | Churchill et al. |
| 4,530,840 A | 7/1985 | Tice et al. |
| 4,542,025 A | 9/1985 | Tice et al. |
| 4,563,489 A | 1/1986 | Urist |
| 4,596,574 A | 6/1986 | Urist |
| 4,619,989 A | 10/1986 | Urist |
| 4,675,189 A | 6/1987 | Kent et al. |
| 4,677,191 A | 6/1987 | Tanaka et al. |
| 4,683,288 A | 7/1987 | Tanaka et al. |
| 4,686,092 A | 8/1987 | Lok et al. |
| 4,742,060 A | 5/1988 | Shiokawa et al. |
| 4,751,225 A | 6/1988 | Nishida et al. |
| 4,758,435 A | 7/1988 | Schaaf |
| 4,761,471 A | 8/1988 | Urist |
| 4,789,732 A | 12/1988 | Urist |
| 4,795,804 A | 1/1989 | Urist |
| 4,798,837 A | 1/1989 | Drabek et al. |
| 4,855,317 A | 8/1989 | Gehret |
| 4,857,335 A | 8/1989 | Bohm |
| 4,857,456 A | 8/1989 | Urist |
| 4,859,657 A | 8/1989 | O'Sullivan et al. |
| 4,871,719 A | 10/1989 | Maienfisch |
| 4,874,749 A | 10/1989 | Mrozik |
| 4,894,373 A | 1/1990 | Young |
| 4,902,296 A | 2/1990 | Bolander et al. |
| 4,904,478 A | 2/1990 | Walsdorf et al. |
| 4,911,931 A | 3/1990 | Baylink |
| 4,916,241 A | 4/1990 | Hayward et al. |
| 4,920,148 A | 4/1990 | Gehret |
| 4,921,697 A | 5/1990 | Peterlik et al. |
| 4,931,287 A | 6/1990 | Bae et al. |
| 4,938,763 A | 7/1990 | Dunn et al. |
| 4,939,131 A | 7/1990 | Benedict et al. |
| 4,942,157 A | 7/1990 | Gall et al. |
| 4,963,582 A | 10/1990 | Sato et al. |
| 4,973,711 A | 11/1990 | Maienfisch |
| 4,978,677 A | 12/1990 | Gehret |
| 5,055,596 A | 10/1991 | Baker et al. |
| 5,077,049 A | 12/1991 | Dunn et al. |
| 5,077,308 A | 12/1991 | Blizzard |
| 5,122,530 A | 6/1992 | Tomioka et al. |
| 5,178,872 A | 1/1993 | Ohtsubo et al. |
| 5,252,701 A | 10/1993 | Jarrett et al. |
| 5,275,820 A | 1/1994 | Chang |
| 5,278,201 A | 1/1994 | Dunn et al. |
| 5,278,202 A | 1/1994 | Dunn et al. |
| 5,288,496 A | 2/1994 | Lewis |
| 5,324,519 A | 6/1994 | Dunn et al. |
| 5,324,520 A | 6/1994 | Dunn et al. |
| 5,340,849 A | 8/1994 | Dunn et al. |
| 5,368,859 A | 11/1994 | Dunn et al. |
| 5,399,582 A | 3/1995 | Dombrowski et al. |
| 5,401,507 A | 3/1995 | Lewis |
| 5,419,910 A | 5/1995 | Lewis |
| 5,427,796 A | 6/1995 | Lewis |
| 5,447,725 A * | 9/1995 | Damani et al. ............. 424/435 |
| 5,478,564 A | 12/1995 | Wantier et al. |
| 5,487,897 A | 1/1996 | Polson et al. |
| 5,540,912 A | 7/1996 | Roorda et al. |
| 5,567,429 A | 10/1996 | Senbo |
| 5,599,552 A | 2/1997 | Dunn et al. |
| 5,599,852 A | 2/1997 | Scopelianos et al. |
| 5,607,686 A | 3/1997 | Totakura et al. |
| 5,609,886 A | 3/1997 | Wantier et al. |
| 5,631,015 A | 5/1997 | Bezwada et al. |
| 5,632,727 A | 5/1997 | Tipton et al. |
| 5,643,595 A | 7/1997 | Lewis |
| 5,654,010 A | 8/1997 | Johnson et al. |
| 5,660,849 A | 8/1997 | Polson et al. |
| 5,686,092 A | 11/1997 | Lewis |
| 5,700,485 A | 12/1997 | Berde et al. |
| 5,702,716 A | 12/1997 | Dunn et al. |
| 5,702,717 A | 12/1997 | Cha et al. |
| 5,707,647 A | 1/1998 | Dunn et al. |
| 5,711,968 A | 1/1998 | Tracy et al. |
| 5,717,030 A | 2/1998 | Dunn et al. |
| 5,725,491 A | 3/1998 | Tipton et al. |
| 5,733,566 A | 3/1998 | Lewis |
| 5,733,950 A | 3/1998 | Dunn et al. |
| 5,736,152 A | 4/1998 | Dunn |
| 5,744,153 A | 4/1998 | Yewey et al. |
| 5,759,563 A | 6/1998 | Yewey et al. |
| 5,780,044 A | 7/1998 | Yewey et al. |
| 5,783,205 A * | 7/1998 | Berggren et al. ........... 424/426 |
| 5,792,469 A * | 8/1998 | Tipton et al. ............... 424/422 |
| 5,824,653 A | 10/1998 | Beuvry et al. |
| 5,990,194 A * | 11/1999 | Dunn et al. ................. 523/113 |
| 6,130,200 A * | 10/2000 | Brodbeck et al. ............. 514/2 |
| 6,136,838 A * | 10/2000 | Chern et al. ................ 514/404 |

OTHER PUBLICATIONS

U.V. Singh, et al., Indian J. of Pharmacology, 29:168–172(1997).

Carrio, et al., Chem. Abstr., 124:37547.

Shah, et al., J. Controlled Release, (1993) 27:139–147.

Lambert and Peck, J. Controlled Release, (1995) 33:189–195.

Shivley, et al., J. Controlled Release, (1995) 33:237–243.

* cited by examiner

180
LIQUID POLYMERIC COMPOSITIONS FOR CONTROLLED RELEASE OF BIOACTIVE SUBSTANCES

CROSS REFERENCE TO RELATED APPLICATION

This application claims priority from and incorporates by reference Chern and Zingerman, U.S. provisional application Serial No. 60/079,574 filed, Mar. 19, 1998.

FIELD OF THE INVENTION

The present invention relates to liquid polymeric compositions; for instance, such compositions for controlled release of at least one bioactive substance, e.g., at least one hydrophobic bioactive substance, such as a liquid polymeric composition which can form a film encapsulated liquid, e.g., in situ and/or which can achieve a long-term sustained release in a patient or host (e.g., animal or human) such as plasma profiles showing high efficacy (greater than about 70%, such as at least about 80%, preferably at least about 90%, e.g., about 100% efficacy for greater than about 12 months and/or plasma levels sustained for at least about 50 or about 60 days or at least about two months or at least about eight weeks, e.g., at least about 90 days or about three months or about 12 weeks or at least about 120 days or about four months or about 16 weeks, or at least about 150 days or about five months or about 20 weeks, or even longer, e.g., up to about a year or more; for instance, from 1 to 12 months.

The present invention further relates to a liquid polymeric composition comprising: (1) about 1–30% w/v bioactive substance (e.g., hydrophobic bioactive substance); (2) about 1–20% w/v of a biologically acceptable "polymer" (including "copolymer", a polymer polymerized by at least two comonomers) (e.g., poly(lactide-co-glycolide) copolymer), for instance, wherein the weight ratio of the polymer to the bioactive substance can be 1:1 or less, e.g., 0.3:1 to 1:1; and (3) at least one lipophilic solvent or a mixture of hydrophilic and lipophilic solvents wherein the volume ratio of the hydrophilic and lipophilic solvents is from about about 80:20 to about 0:100, for instance about 80:20 to about 10:90 or 5:95, hydrophilic and lipophilic solvents, e.g., about 65:35 to about 35:65, and/or wherein the the water immiscible or lipophilic solvent is present in an amount of at least about 16.5% by weight (e.g., including about 16.465% by weight), such as at least about 16.5% to about 45% by weight, for instance at least about 16.5% to about 30% by weight (e.g., at least about 29% by weight) or at least greater than 40% by weight (for instance and at least about 42–45% by weight); e.g., such compositions wherein there is less than 10% of the polymer and 1 to 10% of the bioactive active substance or about less than 7% (e.g., 6.7%) or 5% or less polymer, with the bioactive substance content at less than or equal to about 10% or 5%.

The present invention yet further relates to a liquid polymeric composition consisting essentially of the foregoing, wherein the liquid polymeric composition is capable of forming a film encapsulated liquid, e.g., in situ, and/or having long-term sustained release, wherein the term "consisting essentially of" is used in the sense attributed to it in patent documents, and the term is exclusionary as to ingredients which may impede the capability of the composition to so form a film encapsulated liquid.

The present invention still further relates to methods for making and using such compositions. For example, a method of making such compositions comprising admixing the aforementioned ingredients; for instance, preferably dissolving both the polymer and the bioactive substance (as opposed to suspending, encapsulating, or having present as a solid, the bioactive substance, which, while not necessarily excluded by the invention, may be less preferable to dissolving). Or, a method for using such compositions comprising administering to a patient or host (animal, e.g., mammal such as domesticated animal, for instance companion animal or feedstock animal, or human) an inventive composition.

These and other areas to which the invention relates will be apparent from the following text. Various documents are cited in the following text, without any admission that any of these documents are prior art as to the invention. All documents cited in this text, as well as all documents referenced in documents cited in this text, are hereby incorporated herein by reference.

BACKGROUND OF THE INVENTION

Biodegradable polymers have been used in parenteral controlled release formulations of bioactive compounds. In one approach the polymer is fabricated into microspheres that may be injected via syringe, and the bioative compound is entrapped within the microspheres. This approach has not proved to be practical in part due to the difficulty in the manufacturing procedure for producing sterile and reproducible products, and the high cost of manufacturing. In another approach the biodegradable polymer and the bioactive material are dissolved in a biocompatible water-miscible solvent to provide a liquid composition. When the liquid composition is injected into the body, the solvent dissipates into the surrounding aqueous environment, and the polymer forms a solid depot from which the bioactive material is released.

European Patent Application 0537559 concerns polymeric compositions having a thermoplastic polymer, rate modifying agent, water soluble bioactive material and water-miscible organic solvent. Upon exposure to an aqueous environment (e.g. body fluids) the liquid composition is capable of forming a biodegradable microporous, solid polymer matrix for controlled release of water soluble or dispersible bioactive materials over about four weeks. The thermoplastic polymer may be, among many listed, polylactide, polyglycolide, polycaprolactone or copolymers thereof, and is used in high concentration (45 to 50%). The rate modifying agent may be, among many others listed, glycerol triacetate (triacetin); however, only ethyl heptanoate is exemplified; and the amount of the rate modifying agent is no more than 15%.

Indeed, with respect to the patent literature, reference is made to:

| U.S. PAT. NO. | INVENTOR |
| --- | --- |
| 4,150,108 | Graham |
| 4,329,332 | Couvreur et al. |
| 4,331,652 | Ludwig et al. |
| 4,333,919 | Kleber et al. |
| 4,389,330 | Tice et al. |
| 4,489,055 | Couvreur et al. |
| 4,526,938 | Churchill et al. |
| 4,530,840 | Tice et al. |
| 4,542,025 | Tice et al. |
| 4,563,489 | Urist |
| 4,675,189 | Kent et al. |

| U.S. PAT. NO. | INVENTOR |
| --- | --- |
| 4,677,191 | Tanaka et al. |
| 4,683,288 | Tanaka et al. |
| 4,758,435 | Schaaf |
| 4,857,335 | Bohm |
| 4,931,287 | Bae et al. |
| 5,178,872 | Ohtsubo et al. |
| 5,252,701 | Jarrett et al. |
| 5,275,820 | Chang |
| 5,478,564 | Wantier et al. |
| 5,540,912 | Roorda et al. |
| 5,447,725 | Damani et al. |
| 5,599,852 | Scopelianos et al. |
| 5,607,686 | Totakura et al. |
| 5,609,886 | Wantier et al. |
| 5,631,015 | Bezwada et al. |
| 5,654,010 | Herbert et al. |
| 5,700,485 | Johnson et al. |
| 5,702,717 | Berde et al. |
| 5,711,968 | Tracy et al. |
| 5,733,566 | Lewis |
| 4,938,763 | Dunn et al. |
| 5,077,049 | Dunn et al. |
| 5,278,201 | Dunn et al. |
| 5,278,202 | Dunn et al. |
| 5,288,496 | Lewis |
| 5,324,519 | Dunn et al. |
| 5,324,520 | Dunn et al. |
| 5,340,849 | Dunn et al. |
| 5,368,859 | Dunn et al. |
| 5,401,507 | Lewis |
| 5,419,910 | Lewis |
| 5,427,796 | Lewis |
| 5,487,897 | Polson et al. |
| 5,599,552 | Dunn et al. |
| 5,632,727 | Tipton et al. |
| 5,643,595 | Lewis |
| 5,660,849 | Polson et al. |
| 5,686,092 | Lewis et al. |
| 5,702,716 | Dunn et al. |
| 5,707,647 | Dunn et al. |
| 5,717,030 | Dunn et al. |
| 5,725,491 | Tipton et al. |
| 5,733,950 | Dunn et al. |
| 5,736,152 | Dunn et al. |
| 5,744,153 | Yewey et al. |
| 5,759,563 | Yewey et al. |
| 5,780,044 | Yewey et al. |

These documents tend to provide compositions that form a solid, gel or coagulated mass; for instance, a significant amount of polymer is contemplated in these documents, akin to European Patent Application 0537559.

Mention is also made of: Shah et al (*J. Controlled Release,* 1993, 27:139–147), as relating to formulations for sustained release of bioactive compounds containing various concentrations of poly(lactic-co-glycolic) acid copolymer (PLGA) dissolved in vehicles such as triacetin; Lambert and Peck (*J. Controlled Release,* 1995, 33:189–195), as a study of the release of protein from a 20% PLGA solution in N-methylpyrrolidone exposed to aqueous fluid; and Shivley et al (*J. Controlled Release,* 1995, 33:237–243), as a study of the solubility parameter of poly(lactide-co-glycolide) copolymer in a variety of solvents, and the in vivo release of naltrexone from two injectable implants (5% naltrexone in either 57% PLGA and 38% N-methylpyrrolidone or 35% PLGA and 60% N-methylpyrrolidone).

There is nonetheless a need for long term sustained-release compositions, as well as polymeric compositions which can form film coated or encapsulated liquids.

OBJECTS AND SUMMARY OF THE INVENTION

In contrast to previous compositions, it has surprisingly been found that a polymeric composition containing a substantially greater amount of water immiscible or lipophilic solvent and substantially less polymer than contemplated by the literature results in a formulation which tends to stay as a film-coated (encapsulated) liquid rather than form a solid, gel or coagulated mass (including "pore-containing" solids, gels or masses as in the literature). It does not appear that the use or amount of the lipophilic solvent and the low amount of polymer used in the liquid polymeric formulations of the invention is contemplated by the prior art.

Accordingly, an object of the invention can be any or all of: to provide a liquid polymeric composition including a bioactive substance, for instance, such a composition that has long-term sustained release and/or forms a film-coated or encapsulated liquid, as well as to provide methods for making and/or using such a composition.

The present invention provides liquid polymeric compositions; for instance, such compositions for controlled release of at least one bioactive substance, e.g., at least one hydrophobic bioactive substance, such as a liquid polymeric composition which can form a film encapsulated liquid, e.g., in situ and/or which can achieve a long-term sustained release in a patient or host (e.g., animal or human) such as plasma profiles showing high efficacy (greater than about 70%, such as at least about 80%, preferably at least about 90%, e.g., about 100% efficacy for greater than about 12 months and/or plasma levels sustained for at least about 50 or about 60 days or at least about two months or at least about eight weeks, e.g., at least about 90 days or about three months or about 12 weeks or at least about 120 days or about four months or about 16 weeks, or at least about 150 days or about five months or about 20 weeks, or even longer, e.g., up to about a year or more; or from 1 to 12 months or longer.

The present invention further provides a liquid polymeric composition comprising: (1) 1–30% w/v of at least one bioactive substance (e.g., hydrophobic bioactive substance); (2) 1–20% w/v of at least one biologically acceptable "polymer" (including "copolymer", a polymer polymerized by at least two comonomers) (e.g., poly(lactide-co-glycolide) copolymer), for instance, wherein the weight ratio of the polymer to the bioactive substance can be 1:1 or less, e.g., 0.5:1 to 1:1; and (3) a mixture of at least one hydrophilic solvent and at least one lipophilic solvent, e.g., at least one biologically or physiologically or medically or veterinarily acceptable hydrophilic solvent and at least one biologically or physiologically or medically or veterinarily acceptable lipophilic solvent wherein the volume ratio of the hydrophilic and lipophilic (or hydrophobic) solvents is from about 80:20 to about 0:100, for instance about 80:20 to about 10:90 or 5:95, hydrophilic and lipophilic solvents, e.g., about 65:35 to about 35:65, and/or wherein the water immiscible or lipophilic solvent is present in an amount of at least about 16.5% by weight (e.g., including 16.465% by weight), such as at least about 16.5% to about 45% by weight, for instance at least about 16.5% to about 30% by weight (eg., at least about 29% by weight), or at least about 20% or about 25% by weight to about 30%, 35%, 40% or 45% by weight, or at least greater than 40% by weight (for instance and at least about 42–45% by weight); e.g., such compositions wherein there is less than 10% of the polymer and 1 to 10% of the bioactive active substance or about less than 7% (e.g., 6.7%) or 5% or less polymer, with the bioactive substance content at less than or equal to about 10% or 5%.

The present invention yet further provides a liquid polymeric composition consisting essentially of the foregoing, wherein the liquid polymeric composition is capable of forming a film encapsulated liquid, e.g., in situ, and/or having long-term sustained release, wherein the term "consisting essentially of" is used in the sense attributed to it in patent documents, and the term is exclusionary as to ingredients which may impede the capability of the composition to so form a film encapsulated liquid. Thus, for instance, an agent which would tend to cause the composition, e.g., in situ, to have one or more contrary properties, e.g., an agent which would tend to cause the composition to solidify, such as a curing agent, or to form pores, may not be desired in certain embodiments.

The present invention still further provides methods for making and using such compositions. For example, a method of making such compositions comprising admixing the aforementioned ingredients; for instance, preferably dissolving both the polymer and the bioactive substance (as opposed to suspending, encapsulating, or having present as a solid, the bioactive substance, which, while not necessarily excluded by the invention, may be less preferable to dissolving). Or, a method for using such compositions comprising administering to a patient or host (animal, e.g., mammal such as domesticated animal, for instance companion animal or feedstock animal, or human) an inventive composition.

The invention additionally provides methods consisting essentially of at least one step for making or using such compositions; wherein the liquid polymeric composition is capable of forming a film encapsulated liquid, e.g., in situ, and/or having long-term sustained release, wherein the term "consisting essentially of" is used in the sense attributed to it in patent documents, and the term is exclusionary as to ingredients which may impede the capability of the composition to so form a film encapsulated liquid. Thus, for instance, a step which would tend to cause the composition, e.g., in situ, to have one or more contrary properties, e.g., adding an agent which would tend to cause the composition to solidify, such as a curing agent, or to form pores, may not be desired in certain embodiments.

The bioactive substance may be any biologically agent which is capable of providing a biological, physiological or therapeutic effect in an animal or human. The biologically active agent may be any one or more of known biologically active agents recognized in any document cited herein or otherwise recognized in the art. The agent may also stimulate or inhibit a desired biological or physiological activity within the animal or human, including without limitation, stimulate an immunogenic or immunological response.

Accordingly, the invention provides an in situ formed film coated or encapsulated liquid implant capable of functioning as a delivery system of drugs, medicaments, and other biologically-active agents to tissues adjacent to or distant from the implant site. The biologically-active agent is preferably incorporated into the film coated or encapsulated liquid, and subsequently released into surrounding tissue fluids and to the pertinent body tissue or organ. The composition may be administered to the implant site by any suitable method for applying a liquid, as for example, by means of a syringe, needle, cannula, catheter, pressure applicator, and the like. Exemplary biologically active agents or bioactive substances include, without limitation, fipronil, avermectin, ivermectin, eprinomectin, milbemycin, phenylpyrazole, nodulisporic acid, estradiol benzoate, tremblone acetate, noresthisterone, progesterone an antibiotic such as a macrolide or azalide antibiotic, or a non-steroidal anti-inflamatory drugs (NSAID), or combinations thereof. Thus, an object of the invention can be to provide delivery of at least one active ingredient, regardless of whether the ingredient is water insoluble or immiscible; but, the invention is especially applicable to hydrophobic biologically active substances.

The biologically acceptable polymer can be any biologically acceptable polymer, such as a biologically acceptable polymer recognized in documents cited herein. For instance, the biologically acceptable polymer can have one or more or all of the following characteristics: be bioerodible by cellular action, biodegradable by action of non-living body fluid components, soften when exposed to heat but return to the original state when cooled and are capable of substantially dissolving or dispersing in a water-miscible carrier or solvent to form a solution or dispersion. Upon contact with an aqueous fluid and the polymer are capable of assisting in the formation of the film coated or encapsulated liquid. The kinds of polymers suitable for the present composition generally include any having the foregoing characteristics. Examples are polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malicacid), poly (amino acids), poly(methyl vinyl ether), poly(maleic anhydride), chitin, chitosan, and copolymers, terpolymers, or combinations or mixtures therein. Polylactides, polycaprolactones, polyglycolides and copolymers thereof are preferred polymers, with poly(lactide-co-glycolide) copolymer ("PLGA") highly preferred. The constitution of PLGA can be akin to its use in the Examples below or in documents cited herein.

The solvents can be any biologically or physiologically or medically or veterinarily hydrophobic and water miscible solvents such as those recognized in documents cited herein.

The hydrophilic solvent may be chosen from propylene glycol, PEG, polyglycols such as polyethylene glycol 200, polyethylene glycol 300 and polyethylene glycol 400, di(ethylene glycol)ethyl ether (Transcutol), isopropylidene glycerol(Solketal), dimethyl isosorbide (Arlasolve DMI), propylene carbonate, glycerol, glycofural, pyrrolidones such as N-methyl pyrrolidone and 2-pyrrolidone, isopropylidene glycerol, di(propyleneglycol) methyl ether, and mixtures thereof. Other solvents may also be useful as the hydrophilic solvent. For instance, the hydrophilic solvent can be a $C_2$ to $C_6$ alkanol (e.g., ethanol, propanol, butanol), acetone, alkyl esters such as methyl acetate, ethyl acetate, ethyl lactate, alkyl ketones such as methyl ethyl ketone, dialkylamides such as dimethylformamide, dimethyl sulfoxide, dimethyl sulfone, tetrahydrofuran, cyclic alkyl amides such as caprolactam, decylmethylsulfoxide, oleic acid, propylene carbonate, aromatic amides such as N,N-diethyl-m-toluamide, and 1-dodecylazacycloheptan-2-one. The hydrophilic solvent can be a mixture of solvents.

The lipophilic or non-water-miscible or hydrophobic solvent may be chosen from triethyl citrate, Miglyol 812, Miglyol 840, Crodamol GTCC, triacetin or benzyl benzoate; and additional lipophilic solvents may be used, e.g., hydrophobic rate modifying agents or plasticizers such as fatty acids, triglycerides, triesters of glycerol, oils such as castor oil, soybean oil or other vegetable oils or derivatives thereof such as epoxidized or hydrogenated vegetable oils such as epoxidized soybean oil or hydrogenated castor oil, sterols, higher alkanols (e.g., $C_6$ or higher), glycerin and the like. The lipophilic solvent can be a mixture of solvents.

Other solvents can include: glycol ethers such as propylene glycol monomethyl ether, dipropylene glycol monomethyl ether and diethylene glycol ethyl ether, di(ethylene glycol)ethyl ether acetate, di(propylene glycol)methyl ether (Dowanol DPM), di(propylene glycol)methyl ether acetate, glycerol formal, glycofurol, isopropyl myristate, N,N,-dimethyl acetamide, PEG 300, propylene glycol, and polar, aprotic solvents such as DMSO.

In certain embodiments there can be less than 10% of the polymer and 1 to 10% of the active compound; for instance, the proportion of the PLGA polymer and the active compound is less than or equal to 1:1. (See, e.g., the Example, wherein for instance 0.25 75/25 PLGA was dissolved in glycerol formal to provide a 2.5 ml solution; in a separate flask 75/25 PLGA was dissolved in triacetin to provide a 2.5 ml solution; the two solutions were mixed and added to a flask containing 0.50 g active ingredient which was dissolved into the mixed PLGA solutions; the amount of triacetin present in the formulation to be about 42% by weight; other formulations contain as little as 6.7% and 5% PLGA content with the drug content at 10% or 5%.)

When implanted, i.e., upon injection, the inventive liquid formulation forms what appears to be, from gross examination of the host or patient into which the formulation is implanted, "a semi-solid depot with a skin made of polymer." The depot, though, without necessarily wishing to be bound by any one particular theory, is not necessarily solid or semi-solid (as that term may be usually understood); but rather, is a film coated or encapsulated liquid (the polymer assisting in the skin formation). Over time, depot loses its vehicle(s) (solvent(s)) and degradation of the polymer occurs.

While there is diffusion through the film (typically whitish in color in preferred embodiments), it is believed that there are no pores in the depot; and it likely that the liquid polymeric formulation does not form in situ, a solid, or a coagulated mass or a gelatinous mass. These beliefs are based on the fact that the amount of polymer in the inventive formulation is substantially less than that used in the prior art; the amount of water immiscible or lipophilic solvent present in inventive formulations is substantially greater than any "rate modifying agent" or similar solvent used in the prior art (allowing the core of the depot to remains liquid); and, as the active ingredient diffuses through the film (a very, very thin film, usually whitish in preferred embodiments), the polymer biodegrades. The inventive formulation, is well-suited for delivering lipophilic (hydrophoblic) active ingredients.

These and other embodiments are disclosed or are obvious from and encompassed by, the following Detailed Description.

BRIEF DESCRIPTION OF FIGURES

The following Detailed Description, given by way of example, but not intended to limit the invention to specific embodiments described, may be understood in conjunction with the accompanying Figures, incorporated herein by reference, in which.

DETAILED DESCRIPTION

Figure 1:
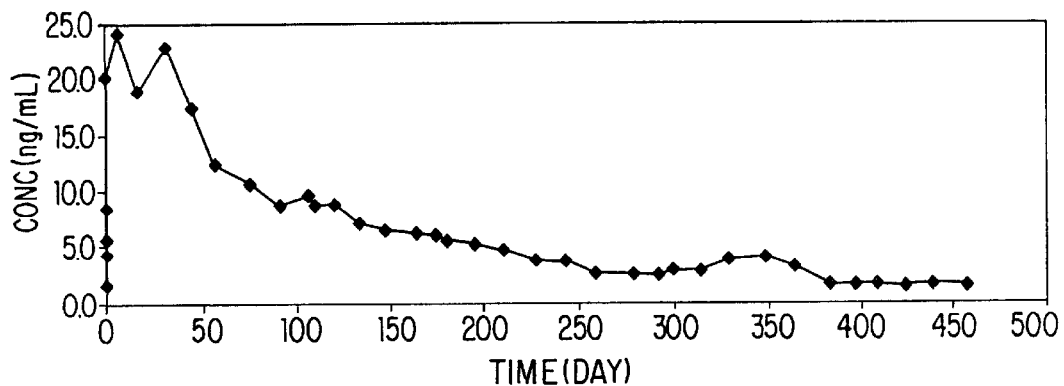
FIG. 1 depicts plasma levels of 6-amino-3-cyano-1-(2,6-dichloro-4-sulfurpentafluorophenyl)-4-(trifluoromethylthio) pyrazole in dogs treated with the formulation of Example 1.
Figure 1:
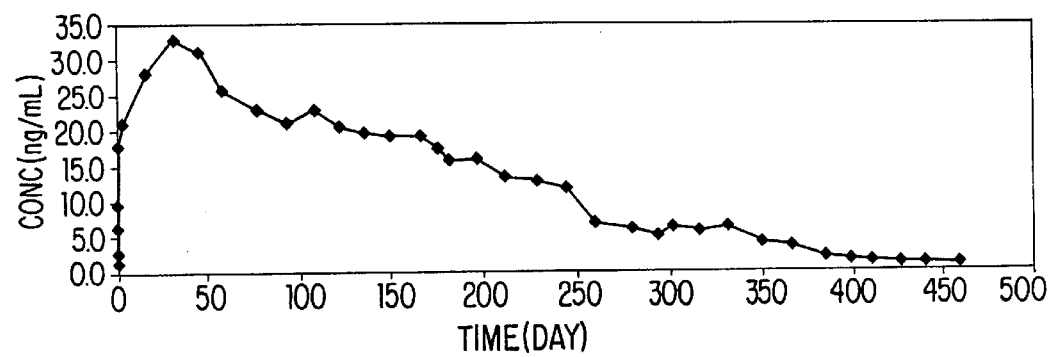
Figure 1:
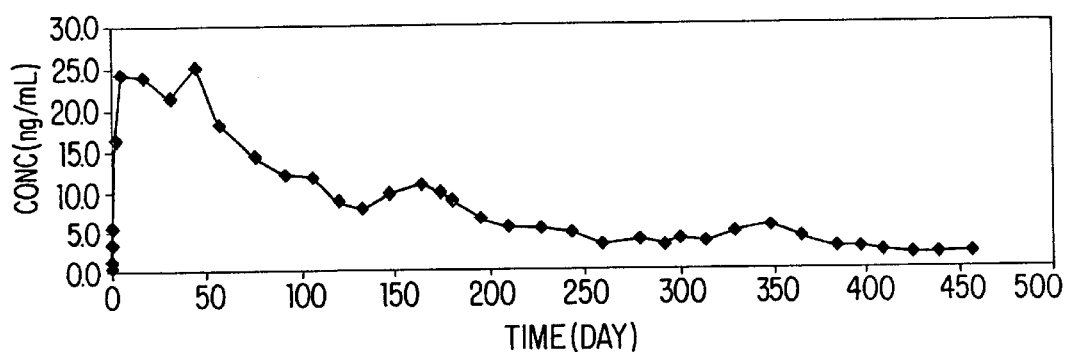

The present invention provides liquid polymeric compositions for delivering bioactive substance(s).

The present invention provides liquid polymeric compositions; for instance, such compositions for controlled release of at least one bioactive substance, e.g., at least one hydrophobic bioactive substance, such as a liquid polymeric composition which can form a film encapsulated liquid, e.g., in situ and/or which can achieve a long-term sustained release in a patient or host (e.g., animal or human) such as plasma profiles showing high efficacy (greater than about 70%, such as at least about 80%, preferably at least about 90%, e.g., about 100% efficacy for greater than about 12 months and/or plasma levels sustained for at least about 50 or about 60 days or at least about two months or at least about eight weeks, e.g., at least about 90 days or about three months or about 12 weeks or at least about 120 days or about four months or about 16 weeks, or at least about 150 days or about five months or about 20 weeks, or even longer, e.g., up to about a year or more; or from 1 to 12 months or longer.

The present invention further provides a liquid polymeric composition comprising: (1) about 1–30% w/v of at least one bioactive substance (e.g., hydrophobic bioactive substance); (2) about 1–20% w/v of at least one biologically acceptable "polymer" (including "copolymer", a polymer polymerized by at least two comonomers) (e.g., poly(lactide-co-glycolide) copolymer), for instance, wherein the weight ratio of the polymer to the bioactive substance can be 1:1 or less, e.g., 0.5:1 to 1:1; and (3) at least one lipophilic solvent or a mixture of at least one hydrophilic solvent and at least one lipophilic solvent, e.g., at least one biologically or physiologically or medically or veterinarily acceptable hydrophilic solvent and at least one biologically or physiologically or medically or veterinarily acceptable lipophilic solvent wherein the volume ratio of the hydrophilic and lipophilic (or hydrophobic) solvents is from about about 80:20 to about 0:100, for instance about 80:20 to about 10:90 or about 80:20 to about 5:95, hydrophilic and lipophilic solvents, e.g., about 65:35 to about 35:65, and/or wherein the the water immiscible or lipophilic solvent is present in an amount of at least about 16.5% by weight (e.g., including 16.465% by weight), such as at least about 16.5% to about 45% by weight, for instance at least about 16.5% to about 30% by weight (e.g., at least about 29% by weight), or at least about 20% or about 25% by weight to about 30%, 35%, 40% or 45% by weight, or at least greater than 40% by weight (for instance and at least about 42–45% by weight); e.g., such compositions wherein there is less than 10% of the polymer and 1 to 10% of the bioactive active substance or about less than 7% (e.g., 6.7%) or 5% or less polymer, with the bioactive substance content at less than or equal to about 10% or 5%.

The present invention yet further provides a liquid polymeric composition consisting essentially of the foregoing, wherein the liquid polymeric composition is capable of forming a film encapsulated liquid, e.g., in situ, and/or having long-term sustained release, wherein the term "consisting essentially of" is used in the sense attributed to it in patent documents, and the term is exclusionary as to ingredients which may impede the capability of the composition to so form a film encapsulated liquid. Thus, for instance, an agent which would tend to cause the composition, e.g., in situ, to have one or more contrary properties, e.g., an agent which would tend to cause the composition to solidify, such as a curing agent, or to form pores, may not be desired in certain embodiments.

The present invention still further provides methods for making and using such compositions, as herein discussed.

The polymers and the solvents employed in the invention can be as herein discussed.

The bioactive substance(s) can be any any biologically agent which is capable of providing a biological, physiological or therapeutic effect in an animal or human. The biologically active agent may be any one or more of known biologically active agents recognized in any document cited herein or otherwise recognized in the art. The agent may also stimulate or inhibit a desired biological or physiological activity within the animal or human, including without limitation, stimulate an immunogenic or immunological response.

The in situ formed implants may also provide a delivery system for biologically-active agents to adjacent or distant body tissues and organs. Biologically-active agents which may be used alone or in combination in the present compositions and implants include medicaments, drugs, or any suitable biologically-, physiologically- or pharmacologically-active substance which is capable of providing local or systemic biological or physiological activity in an animal, including a human, and which is capable of being released from the depot into an adjacent or surrounding aqueous fluid.

The biologically-active agent may be miscible in the polymer and/or solvent to provide a homogenous mixture with the polymer, or insoluble in the polymer and/or solvent to form a suspension or dispersion with the polymer. It is highly preferred that the biologically-active agent be combined with the remaining components of the inventive composition almost immediately prior to administration of the composition to the implant site. It is also preferred that the bioactive agent not be water-miscible, e.g., at best only slightly soluble in water or having low solubility in water or being able to dissolve into the lipophilic (hydrophobic) solvent. It is further preferred that the bioactive agent will not contain functional groups which will interfere the polymer. These conditions are readily determined by those of skill in the art simply by comparing the structure of the bioactive agent and the reacting moieties of the polymer.

The composition and in situ formed implant contain the biologically-active agent in an amount effective to provide a desired biological, physiological, pharmacological and/or therapeutic effect, optionally according to a desired release profile, and/or time duration of release. It is further preferred that the biologically-active agent is included in the polymer composition in an amount effective to provide an acceptable solution or dispersion viscosity.

Suitable biologically-active agents include substances useful in preventing infection at the implant site, as for example, antiviral, antibacterial, antiparasitic, antifungal substances and combinations thereof. The agent may further be a substance capable of acting as a stimulant, sedative, hypnotic, analgesic, anticonvulsant, and the like. The delivery system can contain a large number of biologically-active agents either singly or in combination. Examples of these biologically-active agents include, but are not limited to: Anti-inflammatory agents such as hydrocortisone, prednisone, fludrotisone, triamcinolone, dexamethasone, betamethasone and the like. Anti-bacterial agents such as penicillins, cephalosporins, vancomycin, bacitracin, polymycins, tetracyclines, chloramphenicol, erythromycin, streptomycin, and the like. Antiparasitic agents such as quinacrine, chloroquine, quinine, and the like. Antifungal agents such as nystatin, gentamicin, miconazole, tolnaftate, undecyclic acid and its salts, and the like. Antiviral agents such as vidarabine, acyclovir, ribarivin, amantadine hydrochloride, iododeoxyuridine, dideoxyuridine, interferons and the like. Antineoplastic agents such as methotrexate, 5-fluorouracil, bleomycin, tumor necrosis factor, tumor specific antibodies conjugated to toxins, and the like. Analgesic agents such as salicylic acid, salicylate esters and salts, acetaminophen, ibuprofen, morphine, phenylbutazone, indomethacin, sulindac, tolmetin, zomepirac, and the like. Local anaesthetics such as cocaine, benzocaine, novocaine, lidocaine, and the like. Vaccines, or antigens, epitopes, immunogens of human or animal pathogens, such as hepatitis, influenza, measles, mumps, rubella, hemophilus, diphtheria, tetanus, rabies, polio, as well as veterinary vaccines and the like. Central nervous system agents such as tranquilizers, sedatives, anti-depressants, hypnotics, B-adrenergic blocking agents, dopamine, and the like. Growth factors such as colony stimulating factor, epidermal growth factor, erythropoietin, fibroblast growth factor, neural growth factor, human growth hormone, platelet derived growth factor, insulin-like growth factor, and the like. Hormones such as progesterone, estrogen, testosterone, follicle stimulating hormone, chorionic gonadotrophin, insulin, endorphins, somatotropins and the like. Antihistamines such as diphenhydramine, chlorpheneramine, chlorcyclizine, promethazine, cimetidine, terfenadine, and the like. Cardiovascular agents such as verapamil hydrochloride, digitalis, streptokinase, nitroglycerine paparefine, disopyramide phosphate, isosorbide dinitrate, and the like. Anti-ulcer agents such as cimetidine hydrochloride, sopropamide iodide, propantheline bromide, and the like. Bronchodilators such as metaproternal sulfate, aminophylline, albuterol, and the like. Vasodilators such as theophylline, niacin, nicotinate esters, amylnitrate, minoxidil, diazoxide, nifedipine, and the like.

The bioactive agents which are used in the inventive formulations can be well known to the practitioner to which this invention pertains. Classes of bioactive agents contemplated by the inventive formulations include insecticides, acaricides, parasiticides, growth enhancers, and oil-soluble, nonsteroidal anti-inflammatory drugs (NSAIDs). Specific classes of compounds which fall within these classes include, for example, avermectins, milbemycins, nodulisporic acid and its derivatives, estrogens, progestins, androgens, substituted pyridylmethyl derivatives, phenylpyrazoles, and COX-2 inhibitors.

The avermectin and milbemycin series of compounds are potent anthelmintic and antiparasitic agents against a wide range of internal and external parasites. The compounds which belong to this series are either natural products or are semi-synthetic derivatives thereof. The structure of these two series of compounds are closely related and they both share a complex 16-membered macrocyclic lactone ring; however, the milbemycin do not contain the aglycone substitutent in the 13-position of the lactone ring. The natural product avermectins are disclosed in U.S. Pat. No. 4,310,519 to Albers-Schonberg, et al., and the 22, 23-dihydro avermectin compounds are disclosed in Chabala, et al., U.S. Pat. No. 4,199,569. For a general discussion of avermectins, which include a discussion of their uses in humans and animals, see "Ivermectin and Abamectin," W. C. Campbell, ed., Springer-Verlag, New York (1989). Furthermore, bioactive agents such as avermectins or ivermectin can be used in combination with other bioactive agents; and, with respect to avermectins, ivermectin, and bioactive agent combinations, reference is made to Kitano, U.S. Pat. No. 4,468,390, Beuvry et al., U.S. Pat. No. 5,824,653, von Bittera et al., U.S. Pat. No. 4,283,400, European Patent Application 0 007 812 A1, published Jun. 2, 1980, U.K. Patent Specification 1 390 336, published Apr. 9, 1975, European Patent Application 0 002 916 A2, Ancare New Zealand Patent No. 237 086, Bayer New Zealand Patent 176193, published Nov. 19, 1975, inter alia.

Naturally occurring milbemycins are described in Aoki et al., U.S. Pat. No. 3,950,360 as well as in the various references cited in "The Merck Index" 12$^{th}$ ed., S. Budavari, Ed., Merck & Co., Inc. Whitehouse Station, N.J. (1996). Semisynthetic derivatives of these classes of compounds are well known in the art and are described, for example, in U.S. Pat. No. 5,077,308, U.S Pat. No. 4,859,657, U.S. Pat. No. 4,963,582, U.S Pat. No. 4,855,317, U.S. Pat. No. 4,871,719, U.S. Pat. No. 4,874,749, U.S Pat. No. 4,427,663, U.S. Pat. No. 4,310,519, U.S. Pat. No. 4,199,569, U.S Pat. No. 5,055,596, U.S. Pat. No. 4,973,711, U.S. Pat. No. 4,978,677, and U.S. Pat. No. 4,920,148.

Nodulisporic acid and its derivatives are a class of acaricidal, antiparasitic, insecticidal and anthelminitic agents known to a practitioner of the art. These compounds are used to treat or prevent infections in humans and animals. These compounds are described, for example, in U.S. Pat. No. 5,399,582 and WO 96/29073. Additionally, the compounds can be administered in combination with other insecticides, parasiticides, and acaricides. Such combinations include anthelminitic agents, such as those discussed above which include ivermectin, avermectin, and emamectin, as well as other agents such as thiabendazole, febantel or morantel; phenylpyrazoles such as fipronil; and insect growth regulators such as lufenuron. Such combinations are also contemplated in the present invention.

Generally, all classes of such insecticides may be used in this invention. One example of this class include substituted pyridylmethyl derivatives such as imidacloprid. Agents of this class are described, for example, in U.S. Pat. No. 4,742,060 or in EP 892,060.

Pyrazoles such as phenylpyrazoles and N-arylpyrazoles are another class of insecticides which possess excellent insecticidal activity against all insect pests including blood-sucking pests such as ticks, fleas etc., which are parasites on animals. This class of agents kills insects by acting on the gamma-butyric acid receptor of invertebrates. Such agents are described, for example, in U.S. Pat. No. 5,567,429, U.S. Pat. No. 5,122,530, EP 295,117, and EP 846686 A1 (or Banks GB 9625045, filed Nov. 30, 1996 also believed to be equivalent to U.S. Pat. Ser. No. 309,229, filed Nov. 17, 1997). It would be well within the skill level of the practitioner to decide which individual compounds can be used in the inventive formulations.

Insect growth regulators are another class of insecticides or acaricides, which are also provided for in the inventive formulations. Compounds belonging to this group are well known to the practitioner and represent a wide range of different chemical classes. These compounds all act by interfering with the development or growth of the insect pests. Insect growth regulators are described, for example, in U.S. Pat. No. 3,748,356; U.S. Pat. No. 3,818,047; U.S. Pat. No. 4,225,598; U.S. Pat. No. 4,798,837; and U.S. Pat. No. 4,751,225, as well as in EP 179,022 or U.K. 2,140,010. Again, it would be well within the skill level of the practitioner to decide which individual compounds can be used in the inventive formulation.

Estrogens, progestins, and androgens refers to classes of chemical compounds which are also well known to a practitioner in this art. In fact, estrogens and progestins are among the most widely prescribed drugs and are used, for example, alone or in combination for contraception or hormone replacement therapy in post menopausal women. Estrogens and progestins occur naturally or are prepared synthetically. This class of compounds also includes estrogens or progesterone receptor antagonists. Antiestrogens, such as tamoxifen and clomiphene, are used to treat breast cancer and infertility. Antiprogestives are used as contraceptives and anticancer drugs, as well as to induce labor or terminate a pregnancy.

The androgens and antiandrogens structurally related to the estrogens and progestins as they are also biosynthesized from cholesterol. These compounds are based on testosterone. Androgens are used for hypogonadism and promote muscle development. Antiandrogens are used, for example, in the management of hyperplasia and carcinoma of the prostate, acne, and male pattern baldness as well as in the inhibition of the sex drive in men who are sex offenders. Estrogen, progestins, and androgens are described, for example, in "Goodman & Gilman's The Pharmacological Basis of Therapeutics," 9$^{th}$ ed., J. G. Handman and L. Elimbird, eds., Ch. 57 to 60, pp. 1411–1485, McGraw Hill, New York (1996) or in "Principles of Medicinal Chemistry," 2$^{nd}$ ed., W. O. Foye, ed., Ch. 21, pp. 495–559, Lea & Febiger, Philadelphia (1981).

Estrogens, progestins and androgens are also used in animal husbandry as growth promoters for food animals. It is known in the art that compounds of these classes act as growth-promoting steroids in animals such as cattle, sheep, pigs, fowl, rabbits, etc. Delivery systems to promote the growth of animals are described, for example, in U.S. Pat. No. 5,401,507, U.S. Pat. No. 5,288,469, U.S. Pat. No. 4,758,435, U.S. Pat. No. 4,686,092, U.S. Pat. No. 5,072,716 and U.S. Pat. No. 5,419,910.

NSAIDs are well known in the art. The classes of compounds which belong to this group include salicylic acid derivatives, para-aminophenol derivatives, indole and indene acetic acids, heteroaryl acetic acids, arylpropionic acids, anthranilic acids (fenamates), enolic acids, and alkanones. NSAIDs exert their activity by interfering with prostaglandin biosynthesis by irreversibly or reversibly inhibiting cycloxygenase. Also included are COX-2 inhibitors which act by inhibiting the COX-2 receptor. Compounds of this group possess analgesic, antipyretic and nonsteroidal anti-inflammatory properties. Compounds belonging to these classes are described, for example, in Chapter 27 of Goodman and Gilman on pages 617 to 658 or in Ch. 22 of Foye on pages 561 to 590 as well as in U.S. Pat. No. 3,896,145; U.S. Pat. No. 3,337,570; U.S. Pat. No. 3,904,682; U.S. Pat. No. 4,009,197; U.S. Pat. No. 4,223,299; and U.S. Pat. No. 2,562,830, as well as the specific agents listed in The Merck Index.

Macrolides are a class of antibiotics which contain a many-membered lactone ring to which are attached one or more deoxy sugars. Macrolides are generally bacteriostatic, but have been shown to be bacteriocidal in high concentration against very susceptible organisms. Macrolides are most effective against gram-position cocci and bacilli, although they do possess some activity against some gram-negative organism. Macrolides exert their bacteriostatic activity by inhibiting bacterial protein synthesis by binding reversibly to the 50 S ribosomal subunit. ("Goodman & Gillman's the Pharmacological Basis of Therapeutics," 9th ed., J. G. Hadman & L. E. Limbird, eds., ch. 47, pp. 1135–1140, McGraw-Hill, New York (1996)).

The macrolides as a class are colorless and usually crystalline. The compounds are generally stable in near neutral solution, but they only have limited stability in acid or base solutions. The reason for this is because the glycosidic bonds hydrolyze in acid and the lactone ring saponifies in base ("Principles of Medicinal Chemistry," 2nd ed., W. F. Foye, ed., ch. 31, pp. 782–785, Lea & Febiger, Philadelphia (1981)). Hence, there is a need for pharmaceutical or veterinary compositions for parenteral, e.g., intravenous, intramuscular, subcutaneous, administration of macrolide antibiotics.

The bioactive agent in the present invention can be a macrolide, as macrolides are soluble in many organic solvents but are only slightly water soluble. Solutions of macrolides in organic solvent systems are used in human and veterinary practice for administration by the intramuscular and subcutaneous routes.

Macrolides as a class include the erythromycin and its derivatives as well as other derivatives such as the azalides. Erythromycin (MW 733.94 daltons) is the common name for a macrolide antibiotic produced by the growth of a strain of *Streptomyces erythreous*. It is a mixture of three erythromycins, A, B and C consisting largely of erythromycin A. Its chemical name is (3R*, 4S*, 5S*, 6R*, 7R*, 9R*, 11R*, 12R*, 13S*, 14R*)-4-[(2,6-dideoxy-3-C-methyl-3-O-methyl-α-L-ribo-hexopyranosyl)-oxy]-14-ethyl-7,12,13-trihydroxy-3,5,7,9,11,13-hexamethyl-6[[3,4,6-trideoxy-3-(dimethylamino)-β-D-xylo-hexapyranosyl]oxy] oxacyclotetradecane-2,10-dione, ($C_{37}H_{67}NO_{13}$).

Erythromycin has a broad and essentially bacteriostatic action against many Gram-positive and some Gram-negative bacteria as well as other organisms including mycoplasmas, spirochetes, chlamydiae and rickettsiae. In humans, it finds usefulness in the treatment of a wide variety of infections. It finds wide application in veterinary practice in the treatment of infectious diseases such as pneumonias, mastitis, metritis, rhinitis, and bronchitis in cattle, swine and sheep.

Other derivatives of erythromycins include carbomycin, clarithromycin, josamycin, leucomycins, midecamycins, mikamycin, miokamycin, oleandomycin, pristinamycin, rokitamycin, rosaramicin, roxithromycin, spiramycin, tylosin, troleandomycin, and virginiamycin. As with the erythromycins, many of these derivatives exist as component mixtures. For example, carbomycin is a mixture of carbomycin A and carbomycin B. Leucomycin exists as a mixture of components $A_1$, $A_2$, $A_3$, $A_9$, $B_1$–$B_4$, U and V in various proportions. Component $A_3$ is also known as josamycin and leucomycin V is also known as miokomycin. The major components of the midecamycins is midecamycin A and the minor components are midecamycins $A_2$, $A_3$ and $A_4$. Likewise, mikamycin is a mixture of several components, mikamycin A and B. Mikamycin A is also known as virginiamycin $M_1$. Pristinamycin is composed of pristinamycins $I_A$, $I_B$, and $I_C$, which are identical to virginiamycins $B_2$, $B_{13}$ and $B_2$ respectively, and pristinamycin $II_A$ and $II_B$, which are identical to virginiamycin $M_1$ and 26,27-dihydrovirginiamycin $M_1$. Spiramycin consists of three components, spiromycin I, II, and III. Virginiamycin is composed of virginiamycin $S_1$, and virginiamycin $M_1$. All these components may be used in this invention. Sources of these macrolides are well known to the practitioner and are described in the literature in references such as "The Merck Index," 12th ed., S. Budarari, ed., Merck & Co., Inc., Whitehouse Station, NJ (1996).

The azalides are semisynthetic macrolide antibiotics related to erythromycin A and exhibit similar solubility characteristics. The structure of azithromycin is known. Useful azalide compounds are disclosed in EP 508699, herein incorporated by reference. The corresponding basic and acid addition salts and ester derivatives of the macrolides compounds are also contemplated for use in this invention. These salts are formed from the corresponding organic or inorganic acids or bases. These derivatives include the customary hydrochloride and phosphate salts as well as the acetate, propionate and butyrate esters. These derivatives may have different names. For example, the phosphate salt of oleandomycin is matromycin and the triacetyl derivative is troleandomycin. Rokitamycin is leucomycin V 4-B-butanoate, 3B-propionate.

Other antibiotics may also be used as a bioactive agent in the practice of this invention.

The bioactive agent can be, for example a peptide or protein. The biologically-active agent may also be a substance, or metabolic precursor thereof, which is capable of promoting growth and survival of cells and tissues, or augmenting the activity of functioning cells, as for example, blood cells, neurons, muscle, bone marrow, bone cells and tissues, and the like. For example, the biologically-active agent may be a nerve growth promoting substance, as for example, a ganglioside, phosphatidylserine, a nerve growth factor, brain-derived neurotrophic factor, a fibroblast growth factor, and the like. To promote tissue growth, the biologically-active agent may be either a hard or soft tissue promoting substance or combinations thereof. Suitable tissue growth promoting agents include, for example, fibronectin (FN), endothelial cell growth factor (ECGF), cementum attachment extracts (CAE), human growth hormone (HGH), a Periodontal ligament cell growth factor, fibroblast growth factor (FGF), animal growth hormones, platelet derived growth factor (PDGF), epidermal growth factor (EGF), protein growth factor interleukin-1 (IL-1), transforming growth factor (TGF.beta.-2), insulin-like growth factor II (ILGF-II), human alpha thrombin (HAT), osteoinductive factor (OIF), bone morphogenetic protein (BMP) or protein derived therefrom, demineralized bone matrix, and releasing factors thereof. Further, the agent may be a bone growth promoting substance such as hydroxyapatite, tricalcium phosphate, a di- or polyphosphonic acid, an anti-estrogen, a sodium fluoride preparation, a substance having a phosphate to calcium ratio similar to natural bone, and the like. A bone growth promoting substance may be in the form, as for example, of bone chips, bone crystals or mineral fractions of bone and/or teeth, a synthetic hydroxyapatite, or other suitable form. The agent may further be capable of treating metabolic bone disorders such as abnormal calcium and phosphate metabolism by, for example, inhibiting bone resorption, promoting bone mineralization, or inhibiting calcification. See, for example, U.S. Pat. No. 4,939,131 to Benedict et al., U.S. Pat. No. 4,942,157 to Gall et al., U.S. Pat. No. 4,894,373 to Young, U.S. Pat. No. 4,904,478 to Walsdorf et al., and U.S. Pat. No. 4,911,931 to Baylink, U.S. Pat. No. 4,916,241 to Hayward et al., U.S. Pat. No. 4,921, 697 to Peterlik et al., U.S. Pat. No. 4,902,296 to Bolander et al., U.S. Pat. No. 4,294,753 to Urist, U.S. Pat. No. 4,455,256 to Urist, U.S. Pat. No. 4,526,909 to Urist, U.S. Pat. No. 4,563,489 to Urist, U.S. Pat. No. 4,596,574 to Urist, U.S. Pat. No. 4,619,989 to Urist, U.S. Pat. No. 4,761,471 to Urist, U.S. Pat. No. 4,789,732 to Urist, U.S. Pat. No. 4,795,804 to Urist, and U.S. Pat. No. 4,857,456 to Urist, the disclosures of which are incorporated by reference herein.

Further still, the biologically active agent or bioactive agent can be an antineoplastic, antitumor or anticancer agent.

The biologically-active agent may be included in the compositions in the form of, for example, an uncharged molecule, a molecular complex, a salt, an ether, an ester, an amide, or other form to provide the effective biological or physiological activity.

With respect to biologically active agents useful in the practice of this invention, reference is also made to the U.S.

and PCT applications of Williams and Chern, "Long Acting Injectable Formulations Containing Hydrogenated Castor Oil," filed Sep. 14, 1998, U.S. Ser. No. 09/15277 and PCT application No. US98/190, and claiming priority from U.S. application Serial No. 60/067,374, incorporated herein by reference.

From the foregoing, the bioactive agent can be varied. The amount suitable for use in a formulation according to the invention can be determined by the skilled artisan without any undue experimentation from the knowledge in the art, and this disclosure, taking into consideration factors typically considered by those skilled in the medical, veterinary or pharmaceutical arts, such as the species involved, the age, weight, general health, and sex of the host or patient or animal or human, and the condition being treated and the $LD_{50}$ and other characteristics of the bioactive substance(s).

Thus, administration of the composition of the invention ultimately will be accomplished according to the wisdom and protocol of the patient's or host's or animal's or human's attending health care professional such as a physician or veterinarian, or if appropriate, a dentist. Choice of the particular composition will depend upon the malcondition or condition to be treated, which choice will be made by the attending health care professional. Application by syringe, or other means for applying a liquid to or into a tissue may be employed. The amounts and concentrations of composition administered to the patient, host, animal or human will generally be sufficient to accomplish the task intended. For administration of bioactive agent, the amounts and release rates will follow recommendations of the manufacturer of the bioactive agent. Generally, the concentration of bioactive agent in the liquid polymer formulation can be from 0.01 mg per g of mixture to 400 mg per g of mixture.

In certain embodiments, the present invention provides a liquid polymeric composition for controlled release of hydrophobic bioactive substances comprising:

(a) 1 to 30% w/v of a hydrophobic bioactive substance;

(b) 1 to 20% w/v of a poly(lactide-co-glycolide) copolymer;

(c) a mixture of hydrophilic and lipophilic solvents wherein the volume ratio of the hydrophilic and lipophilic solvents is from about 80:20 to about 5:95.

In a certain preferred embodiment, the bioactive substance, e.g., at least one hydrophobic bioactive substance, is present in a concentration of 1 to 10% w/v; more preferably 5 to 10% w/v.

In another preferred embodiment, polymer, e.g., the poly(lactide-co-glycolide) copolymer, is present in a concentration of 1 to 10% w/v; more preferably 1 to 5% w/v.

In another preferred embodiment, the weight ratio of the polymer, e.g., poly(lactide-co-glycolide) copolymer, to the bioactive substance, e.g., at least one hydrophobic bioactive substance, is 1:1 or less; more preferably 0.5:1 to 1:1

In yet another preferred embodiment, the volume ratio of the hydrophilic and lipophilic solvents is from about 65:35 to about 35:65.

In another aspect of the present invention there is provided a liquid polymeric composition for controlled release of hydrophobic bioactive substances comprising:

(a) a hydrophobic bioactive substance;

(b) a poly(lactide-co-glycolide);

(c) a mixture of glycerol formal and triacetin.

In another aspect of the present invention there is provided a method for controlled release of at least one bioactive substance, e.g., at least one hydrophobic bioactive substance, which comprises injecting an animal with a liquid polymeric composition described herein.

In addition to the foregoing, as used herein the following terms are as defined below, unless otherwise specified:

"Polymer" includes "copolymers"; a "copolymer" is a polymer from the polymerization of at least two monomers; and thus, a "copolymer" can include a "terpolymer" or a polymer from two, three or more monomers.

"Hydrophobic bioactive substance" means compounds useful in human or animal health having a water solubility of <2%, preferably <1%, at room temperature. Examples of hydrophobic bioactive substances suitable for the present invention include, but are not limited to, avermectins (e.g. ivermectin, eprinomectin, etc), milbemycins, phenylpyrazoles, nodulisporic acid and derivatives such as those disclosed in U.S. Pat. No. 5,399,582 and WO96/29073, estradiol benzoate, trenbolone acetate, progesterone, norethisterone, non-water-soluble NSAIDs, etc.

"Poly(lactide-co-glycolide)" means a copolymer of lactic and glycolic acids having a lactide:glycolide ratio of from 95:05 to 50:50, preferably 75:25 to 65:35. The lactic acid can be d- or l- or dl-. The copolymer may be a single copolymer of a mixture of copolymers within the above-defined parameters.

"Hydrophilic solvent" means water miscible solvents, preferably those when mixed with water in a ratio from 1:9 to 9:1 form a single-phase solution. Examples of hydrophilic solvents suitable for the present invention include, but not limited to glycerol formal, glycofural, N-methyl pyrrolidone, 2-pyrrolidone, isopropylidene glycerol, di(propylene glycol) methyl ether, and mixtures thereof.

"Lipophilic solvent" means water immiscible solvents, preferably with a solubility in water of less than 10% at room temperature. Examples of lipophilic solvents suitable for the present invention include, but not limited to triacetin, benzyl benzoate, and mixtures thereof.

The liquid composition of the present invention is capable of providing prolonged drug release once it is injected, without the bursting drug release typical of existing liquid injectable formulations. Without being bound by theory, it is hypothesized that upon injection the liquid formulation of the present invention initially forms a depot with a skin made of the polymer surrounding a liquid core (which may appear "semi-solid"), while some of the hydrophilic solvent diffuses away from the depot carrying the dissolved bioactive compound with it. The initial drug release from the depot is mostly by permeation through the skin. The permeability of the skin and the rate of initial drug delivery are controlled by the proportions of the hydrophilic and lipophilic solvents in the liquid vehicle, at given polymer and drug concentrations. Over time, the depot loses its liquid vehicles and degradation of the polymer gradually becomes a significant drug-release mechanism. Proper adjustment of the liquid formulation composition thus allows overlap of the permeation-controlled and erosion-controlled drug delivery and results in a flattened and extended drug-release profile over a long period of time. And thus, the depot biodegrades, without wishing to necessarily be bound by any one particular theory, without necessarily forming a solid or other physical form associated with prior art compositions.

The presence of the lipophilic solvent in the liquid composition of the present invention reduces the initial delivery of bioactive compound, thus eliminating the bursting drug release typical of existing liquid injectable formulations where a large portion of hydrophilic vehicle is used. The presence of the hydrophilic solvent facilitates the formation of the polymer skin while preventing precipitation of the bioactive compound, thus allowing a much higher level of drug delivery than possible when only lipophilic vehicles are used. In the present invention, the prefered hydrophilic:lipophilic solvent ratio is between 80:20 to 20:80, most preferably between 65:35 to 35:65.

Other factors that may influence the performance of the present liquid formulation include: (1) the polymer, e.g., PLGA polymer concentration, (2) the relative proportion of the bioactive compound and the polymer, (3) the comonomer, e.g., lactide:glycolide raito in the polymer, and (4) the molecular weight of the polymer. Factors (3) and (4) were well known in the art (see documents cited herein). This invention, however, differs considerably from the existing art, especially in aspects (1) and (2).

The liquid formulation of the present invention contains no more than 20% polymer, e.g., PLGA polymer, preferably less than 10% of the polymer, in order to maintain a relatively constant drug delivery rate at the same time ensuring a reasonably long drug delivery duration (greater than 3 months). The concentration of polymer, e.g., PLGA in the present formulation is therefore in sharp contrast to the known formulations where substantially larger proportion of polymer such as PLGA polymer is prescribed. The concentration of the bioactive substance in the liquid formulation may be from 1% to 30%. Preferably, the proportion of polymer, e.g., PLGA polymer relative to the bioactive compound is less than or equal to 1:1; a ratio that is also substantially below those commonly prescribed. Within the range described herein, higher polymer concentrations reduce the drug delivery rate, and increasing the polymer::bioactive compound ratio also reduces the delivery rate.

The liquid composition may be prepared by dissolving all the solid ingredients in the vehicle under normal manufacturing conditions used for sterile injectable products. The present composition may contain additional inert substances commonly used in parenteral formulations including, but not limited to, antimicrobial agents, antioxidants, and the like.

The instant liquid compositions are administered to a warm-blooded animal such as human, cattle, sheep, pigs, dogs, horses, cats, and the like (e.g., mammals such as humans and companion and feedstock animals) by intramuscular or subcutaneous injection. The formulations will generally be prepared to contain from 1 to 30%, preferably from 1 to 10% of the bioactive compound. For instance, at a preferred dose volume of about 1 ml to treat a cattle of 50 kg body weight the formulation contains from 50 to 100 mg of avermectin compound per ml of solution or about 5 to 10% w/v. However, depending upon the activity of the compound and the animal being treated, concentrations as low as 1% of bioactive compound are usable.

The following examples are provided to illustrate the invention and are not to be construed as limiting the invention in any manner.

EXAMPLE 1

Preparation of Long-Acting Injectable Formulation Containing 6-amino-3-cyano -1-(2,6-dichloro-4-sulfurpentafluorophenyl)-4-(trifluoromethylthio) pyrazole Poly(DL-lactide/glycolide) 75/25 (PLGA, 0.25 g) was dissolved in sufficient glycerol formal to provide a 2.5 ml solution. In a separate flask poly(DL-lactide/glycolide) 75/25 (0.25 g) was dissolved in sufficient triacetin to provide a 2.5 ml solution. The two PLGA solutions were mixed well and added to a flask containing the active ingredient (0.50 g). The contents of the flask were mixed until the active ingredient dissolved, and the resulting solution was sterile filtered into a vial and sealed.

EXAMPLE 2

Preparation of Long-Acting Injectable Formulation Containing Ivermectin

The general procedure of Example 1 was followed to provide the following ivermectin formulations:

| No. | drug content % w/v | PLGA content % w/v | Solvent ratio TA/GF* | polymer type |
|---|---|---|---|---|
| 1 | 10 | 10 | 20/80 | 7525 |
| 2 | 10 | 10 | 35/65 | 7525 |
| 3 | 10 | 6.7 | 50/50 | 7525 |
| 4 | 10 | 5 | 50/50 | 7525 |
| 5 | 10 | 5 | 50/50 | 5050 |

*TA = triacetin; GF = glycerol formal

For comparison purposes, i.e., to illustrate just how much more solvent is used in the present invention in comparison to prior art compositions: In preparation 1 of this example, the triacetin, the lipophilic solvent, is present at about 16.45% by weight. In preparation 2 of this example, the triacetin, the lipophilic solvent is present at about 29% by weight. In preparation 3 of this example, the triacetin, the lipophilic solvent is present at about 42% by weight. In preparation 4 of this example, the triacetin, the lipophilic solvent, is present at about 43% by weight.

EXAMPLE 3

Preparation of Long-Acting Injectable Formulation Containing Eprinomectin

The general procedure of Example 1 was followed to provide the following eprinomectin formulations:

| No. | drug content % w/v | PLGA content % w/v | Solvent ratio TA/GF | polymer type |
|---|---|---|---|---|
| 1 | 10 | 10 | 50/50 | 7525 |
| 2 | 5 | 5 | 50/50 | 6535 |

For comparison purposes, i.e., to illustrate just how much more solvent is used in the present invention in comparison to prior art compositions: In preparation 2 of this example, the triacetin, the lipophilic solvent, is present at about 45% weight percent. And, it is noted that the lipophilic solvent, in preparations according to this invention can be 100% of the volume of solvents present, as discussed in the foregoing general description.

EXAMPLE 4

Activity of Long-Acting Injectable Formulation Containing 6-amino-3-cyano -1-(2,6-dichloro-4-sulfurpentafluorophenyl)-4-(trifluoromethylthio) pyrazole Against Fleas in Dogs Three beagle dogs were treated with the formulation of Example 1 at a single subcutaneous dose of 10 mg/kg. Dogs were fasted for at least 6 hours before and 6 hours after the treatment. On day 1 (day 0=day of drug administration) the animals were infested with approximately 100 fleas. Animals were combed and fleas counted and removed approximately 48 hours after infestation. Animals were infested on days 12 and 26, and combed and fleas, counted and removed approximately 48 hours after infestation. Infestation/counting were repeated approximately monthly.

Blood samples were collected from animals on Day 0 at 1, 2, 3 and 6 hours after treatment, on Day 1 at 24 hours after treatment, and if emesis was observed. Blood samples were also collected when flea counts were determined. Animals were observed hourly for 6 hours post treatment for emesis. Close to 100% efficacy has been demonstrated for >12 months without any occurrence of emesis in the treated animals. The plasma level profiles for the individual dogs are shown as FIG. 1.

Example 5

Plasma Level Profiles of Long-Acting Ivermectin Formulations in Cattle

Figure 2:
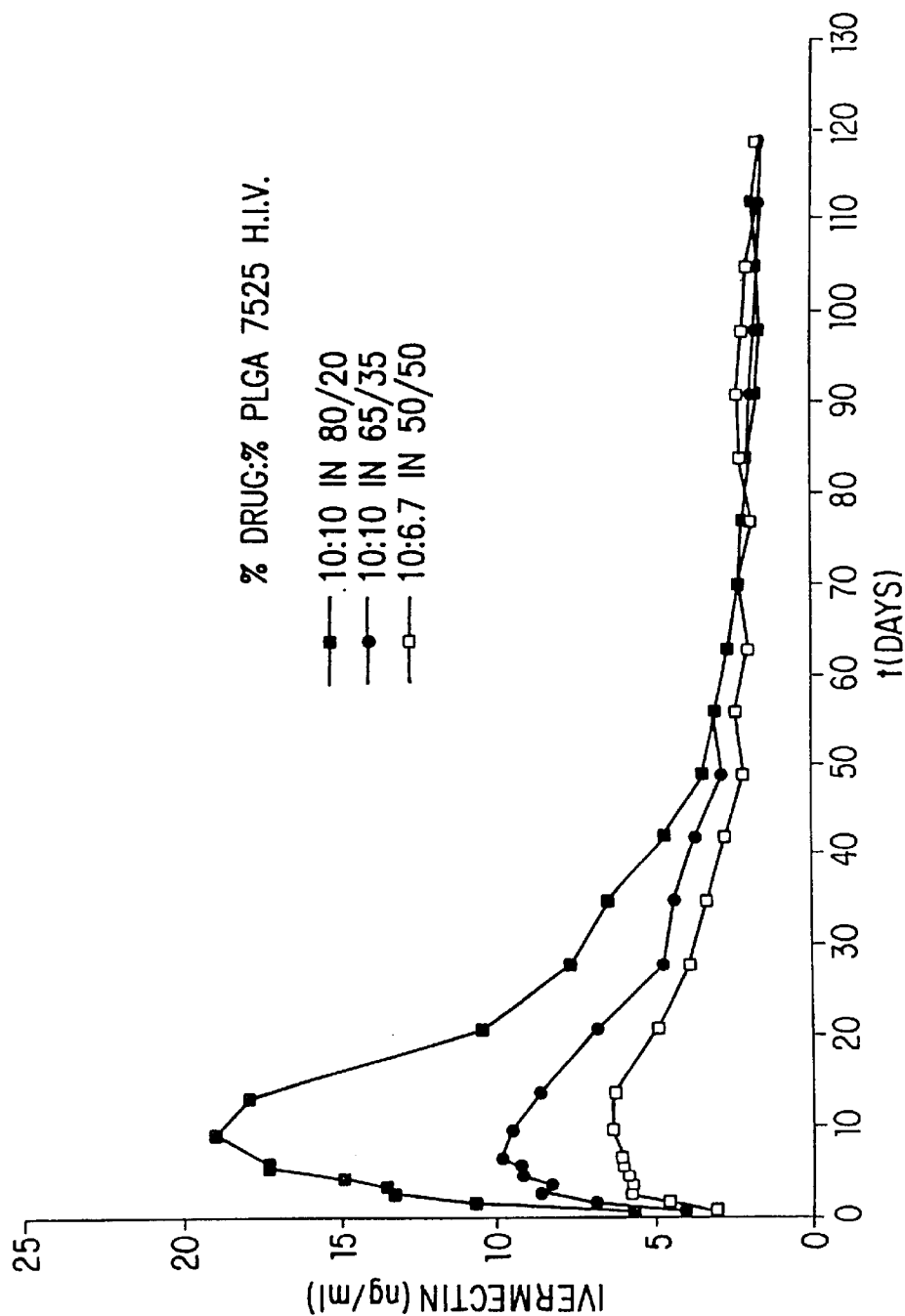
FIG. 2 depicts plasma levels of ivermectin in cattles treated with three of the ivermection formulations of Example 2; and, FIG. 3 depicts plasma levels of eprinomectin in swine treated with eprinomectin formulations of Example 3.

Plasma levels of ivermectin were determined in healthy cattles treated with ivermectin formulations 1, 2 and 3 of Example 2. Each formulation was given to a group of five cattles (generally weighing 125 to 250 kg) as a single subcutaneous injection dosed at 1 mg/kg. Ten ml haparinized blood samples were collected from each treated animal on Days 1–7 (daily), 10, 14, and weekly thereafter for 15 weeks. The plasma level profiles (average of the five animals in each group) are shown in FIG. 2.

Example 6

Plasma Level Profiles of Long-Acting Eprinomectin Formulation in Swine

Figure 3:
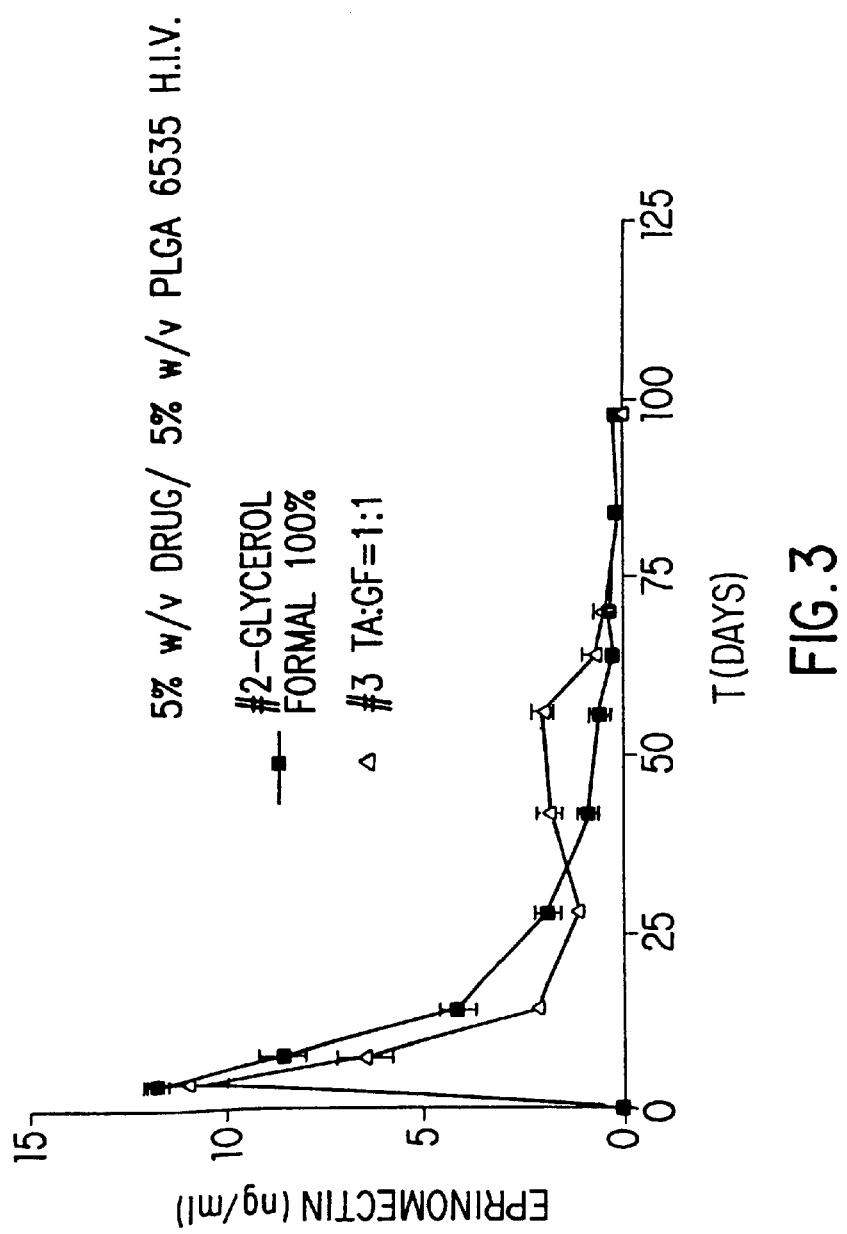

Plasma levels of eprinomectin were determined in swine treated with eprinomectin formulation 2 of Example 3. Three swine (inoculated with 2,000 infective ova of Trichuris suis on day -50, and orally with 15,000 infective larvae of Oesophagostomum sp. on day 0) were injected subcutaneously with formulation 2 of Example 3 at a dose of 1.5 mg/kg. Ten ml blood samples were collected from each animal on days 3, 7 and weekly thereafter. The plasma level profile is shown in FIG. 3 (with alternate formulation of drug/PLGA in 100 glycerol formal).

Having thus described in detail preferred embodiments of the present invention, it is to be understood that the invention defined by the appended claims is not to be limited to particular details set forth in the above description as many apparent variations thereof are possible without departing from the spirit or scope of the present invention.

What is claimed is:

1. A liquid polymeric composition for controlled release of eprinomectin consisting essentially of:
   (a) 1 to 10% of eprinomectin;
   (b) 1 to 10% of a poly(lactide-co-glycolide) copolymer; wherein the weight ratio of the poly(lactide-co-glycolide) copolymer to the eprinomectin is 1:1 or less and the ratio of lactide:glycolide of the poly(lactide-co-glycolide) copolymer is from about 75:25 to about 65:35; and
   (c) at least one lipophilic solvent or a mixture of hydrophilic and lipophilic solvents, wherein the volume ratio of the hydrophilic and lipophilic solvents is from about 80:20 to about 5:95.

2. The composition of claim 1 wherein the lipophilic solvent is triacetin.

3. The composition of claim 2 wherein the hydrophilic solvent is N-methyl pyrrolidone.

4. The composition of claim 3 consisting essentially of:
   (a) 1 to 10% of eprinomectin;
   (b) 1 to 10% of a poly(lactide-co-glycolide) copolymer; wherein the weight ratio of the poly(lactide-co-glycolide) copolymer to the eprinomectin is 1:1 or less and the ratio of lactide:glycolide of the poly(lactide-co-glycolide) copolymer is from about 75:25 to about 65:35; and
   (c) N-methyl pyrrolidone and triacetin, wherein the volume ratio of the N-methyl pyrrolidone and triacetin is from about 80:20 to about 5:95.

5. The composition of claim 4 wherein (a) consists essentially of about 5% eprinomectin.

6. The composition of claim 5 wherein the ratio of lactide:glycolide of the poly(lactide-co-glycolide) copolymer is about 75:25.

7. The composition of claim 6 wherein (b) is 5% poly(lactide-co-glycolide) copolymer.

8. The composition of claim 2 consisting essentially of:
   (a) 1 to 10% of eprinomectin;
   (b) 1 to 10% of a poly(lactide-co-glycolide) copolymer; wherein the weight ratio of the poly(lactide-co-glycolide) copolymer to the eprinomectin is 1:1 or less and the ratio of lactide:glycolide of the poly(lactide-co-glycolide) copolymer is from about 75:25 to about 65:35; and
   (c) triacetin.

9. The composition of claim 8 wherein (a) consists essentially of about 5% eprinomectin.

10. The composition of claim 9 wherein the ratio of lactide:glycolide of the poly(lactide-co-glycolide) copolymer is about 75:25.

11. The composition of claim 10 wherein (b) is 5% poly(lactide-co-glycolide) copolymer.

12. The composition of claim 1 wherein the hydrophilic solvent is N-methyl pyrrolidone.

13. A method for the controlled release of eprinomectin in a mammal which comprises injecting said mammal with the composition of any one of claims 1–12.

14. The method of claim 13 wherein the mammal is a bovine.

15. The method of claim 13 wherein the mammal is an ovine.

16. The method of claim 13 wherein the mammal is a canine.

* * * * *